United States Patent [19]

Dobrescu

[11] Patent Number: 4,465,665

[45] Date of Patent: Aug. 14, 1984

[54] **DETOXIFIED *E. COLI* NEUROTOXIN, PREPARATION THEREOF AND IMMUNOLOGICAL PREPARATIONS CONTAINING IT**

[75] Inventor: Lucia Dobrescu, Brussels, Belgium

[73] Assignee: Smithkline-Rit, Belgium

[21] Appl. No.: 354,880

[22] Filed: Mar. 4, 1982

[51] Int. Cl.$^3$ .................. A61K 39/108; C07G 7/00
[52] U.S. Cl. ................................. 424/92; 424/88; 260/112 R
[58] Field of Search ............... 424/88, 92; 260/112 R

[56] References Cited

U.S. PATENT DOCUMENTS

| | | | |
|---|---|---|---|
| 3,983,229 | 9/1976 | Relyveld | 424/92 |
| 4,136,181 | 1/1979 | Dorbrescu | 424/92 |

OTHER PUBLICATIONS

Schimmelpfennig et al., Zbl. Vet. Med. 29, 25–32, (1978).
Relyveld et al., Ann. Immunol. Hung. 17:21–31, (1973).
Relyveld, C. R., Acad. Sci. (D) 277(6):613–616, (1973).
Relyveld et al., Dev. Biol. Stand 27:263–248, (1974).
Relyveld, Toxicon 1976 (published 1978) Supplement 1 (Toxins; Animal, Plant and Microbiol), pp. 1045–1065.
Willinger et al., Proc. Symp. XII International Cong. Microbiol., Munich, Sep. 3–8, 1978.
Sojka, Res. Vet. Sci. 1:17–27, (1960).
Schimmelpfennig, Zbl. Vet. Med. (B) 18:622–633, (1971).
Sojka, E. coli in Domestic Animals and Poultry edit by Commonwealth Agricultural Bureau, p. 124, (1965).
E. Kauker, Deuts, Tieraerzt. Wochensch. 78:182–184, (1971).
K. Lutter, Monatsh. Veterinaermed. 29:694–699, (1974).
Schimmelpfennig, Fortschr. Vet. Med. 13: 49–50, (1970).
Symp. Series Immunobiol. Standard 6: 177–180, (1967).

*Primary Examiner*—Blondel Hazel
*Attorney, Agent, or Firm*—Edward T. Lentz; Janice E. Williams; Alan D. Lourie

[57] ABSTRACT

Detoxified but still immunogenic *E. coli* neurotoxin is prepared by bringing *E. coli* neurotoxin into contact with glutaraldehyde in mild operative conditions, the reaction being stopped where no more than 90% of the neurotoxin are inactivated.

The obtained detoxified neurotoxin is valuable for immunizing piglets against oedema disease.

6 Claims, No Drawings

DETOXIFIED E. COLI NEUROTOXIN, PREPARATION THEREOF AND IMMUNOLOGICAL PREPARATIONS CONTAINING IT

The present invention relates to a detoxified E. coli neurotoxin, to the preparation thereof and to immunological preparations containing it.

It is known that a specific toxin named neutrotoxin and elaborated by pathogen strains of Escherichia coli is the aetiologic agent of a severe piglet disease named piglet oedema disease.

Oedema disease of piglets also known "bowel oedema" or "enterotoxemia" is an acute disease widespread in most countries and responsible for 5 to 80% of piglets deaths. The disease appears within the two weeks following weaning of the piglet and its clinical symptoms are ataxia, convulsions, partial or complete paralysis, oedema of the subcutis in the forehead and eyelids, anatomopathological features being oedema of various organs, principally the stomach wall, the mesentery of the spiral colon and the brain.

The neurotoxin is produced by different and well known E. coli serotypes.

In Res. Vet. sci. 1:17-27, 1960 W. J. Sojka describes the most common E. coli serotypes isolated in piglet oedema disease cases and in Zbl. Vet. Med. (B) 18:622-33, 1971 H. Schimmelpfennig indicates that the neurotoxin is produced by the predominant E. coli serotypes isolated from oedema disease in piglets, i.e. the 0138, 0139 and 0141 serotypes.

Upon infection by such E. coli strain, the neurotoxin is released and adsorbed in the intestine of the piglet, causing a general arteriopathy which is responsible for nervous symptoms and oedema.

Active immunization against piglet oedema disease has been attempted with various E. coli preparations consisting of either whole E. coli organisms or lysates thereof (W. J. Sojka, "E. coli in domestic animals and poultry" edited by the Commonwealth Agricultural Bureau, 1965, p. 124; E. Kauker, Deuts. Tieraerzt. Wochensch. 78:182-84, 1971 and K. Lutter, Monatsh. Veterinaermed. 29:694-99, 1974) but these preparations either fail to protect the piglets or only induce a serotype specific immunity corresponding to the E. coli serotype used in the preparation.

U.S. Pat. No. 4,136,181 relates to vaccines which are effective against piglet oedema disease; these vaccines comprise partially purified neurotoxin supplemented with an adjuvant and they are administered by intramuscular or subcutaneous route.

In a paper entitled "Studies on the oedema disease producing toxin of Escherichia coli" (Advances in Vet. Med. Suppl. to Sbl. Vet. Med. 29:25-32, 1978), H. Schimmelpfennig and R. Weber report that "treating the toxins with formaldehyde resulted in complete detoxification but the formalin treated toxins did not show an improved antibody response" and these authors conclude that "there is no evidence that a formol-toxoid is formed". Moreover, the results indicate that, when compared to the natural neurotoxin, the formalin treated toxin have lost in a significant manner the ability of stimulating the production of neutralizing antibodies.

U.S. Pat. 3,983,229 relates to a process for preparing vaccines which consists in bringing into contact a toxic product with glutaraldehyde in mild operative conditions and in stopping the reaction as soon as the inactivation stage is reached.

I have found and this is the object of the present invention that, when treating E. coli neurotoxin with glutaraldehyde in mild operative conditions —i.e. for instance treating an aqueous solution of E. coli neurotoxin which titrates 57 mice $ED_{50}$/ml with a 0.01 M aqueous solution of glutaraldehyde at room temperature — and stopping the reaction when a toxin inactivation level inferior to 90% and preferably comprised between 70 and 90% of the neurotoxin itself is reached —i.e. for a period comprised between 5 minutes and 2 hours —a product herein named 'detoxified neurotoxin' is obtained which is substantially non toxic but still highly immunogenic and therefore valuable for immunizing young (i.e. about one week old) piglets against oedema disease.

Glutaraldehyde is an agent which is already known to react with antigens, forming with them polymeric cross-linked reaction products and the technique of inactivation treatment by glutaraldehyde is also known in the art, including the methods for stopping the inactivation reaction; said methods involve for instance the addition of a reaction blocking agent such as an inorganic salt (e.g. sodium bisulfite) or an amino-acid (preferably lysine or glycin).

The detoxified E. coli neurotoxin of the invention is more innocuous than the purified neurtotoxin of U.S. Pat. No. 4,136,181 and said purified neurotoxin can be used as starting material for the preparation of the detoxified neurotoxin of this invention.

Surprisingly, the immunogenic properties of the detoxified neurotoxin of the invention sharply contrast with glutaraldehyde treated products showning an inactivation level higher than 90% which are not immunogenic.

For immunizing young piglets against oedema disease, the detoxified neurotoxin is formulated into a pharmaceutical composition for intramuscular or subcutaneous route, preferably with an adjuvant and optimally supplemented with an antiseptic such as thiomersal. Adequate adjuvants are those of the group consisting of aluminium hydroxide and aluminium phosphate, e.g. Alhydrogel (an aluminium hydroxide gel manufactured and sold by Superfos Export Co., Copenhagen, Denmark) and the detoxified neurotoxin/adjuvant ratio is preferably calculated for maximum adsorption on the adjuvant, as indicated for instance in Symp. Series Immunobiol. Standard. 6:177-180, 1967).

The invention is illustrated by the following examples which do not limit the scope of the invention; for instance, in the herein examplified neurotoxin production, an E. coli serotype 0139 strain isolated from a clinical infection case is used and it is obvious that any other E. coli strain known as neurotoxin producer can also be used for the same purpose.

EXAMPLE 1

Neurotoxin Preparation (a) Seed Preparation

A sample of an E. coli strain serotype 0139 (named RIT 4349) isolated from a typical piglet oedema disease case and maintained in freeze-dried state is rehydrated with sterile saline and incubated for 18 hours at 37° C. in Petri dishes containing each 20 ml of Tryptose-Agar solid medium prepared by mixing 26 g of Tryptose broth, 30 g of Agar Difco (Tryptose broth and Agar Difco are products manufactured and sold by Difco Labs) and water up to one liter, the mixture being heated for 45 minutes at 115° C.

A liquid culture medium is then prepared as follows: Proteose peptone No. 3 (a product manufacturee and sold by Difco Labs) 30 g, yeast extract (4 g) and dextrose (5 g) are dissolved in one liter of water at 60° C. After cooling, NaCl (5 g), NaHPO$_4$ (5.05 g) and KH$_2$PO$_4$ (1.2 g) are added thereto. The medium, the pH of which is 6.9–7.0 is filtered on Seitz EKS filter and distributed into 100 ml culture flasks.

These culture flasks are inoculated with the colonies obtained on Petri dishes, using one colony per 20 ml of above liquid medium and incubated for six hours at 37° C. with shaking on rocking shelves (22 to 24 rockings per minute).

(b) *E. coli* production and neurotoxin extraction

Six milliliter aliquots of the *E. coli* containing culture medium (i.e. about $6.10^9$ bacteria) are inoculated into production flasks containing 300 ml of same liquid medium and the cultures are incubated for one day with shaking on rocking shelves (22 to 24 rockings per minute).

The harvests of five production flasks (one series) are pooled and each series of harvests is centrifuged for two hours at 2,000 g, the sediment is resuspended in 150 ml of distilled water.

The cell suspension is sonicated for 30 minutes in a Branson Europa sonicator model J 22 (Branson Europa N. V., Soest, The Netherlands), the medium being kept in a melting ice bath.

After disruption of the cells, the suspension is centrifuged for two hours at 2,000 g at 5° C. in order to eliminate the cell debris. The supernatant is passed through a 0.45 micron Millipore sterilizing filter (Millipore is a trademark of Millipore Corporation) to yield 100 ml of filtrate the titre of which (determined by the Reed and Muench endpoint method) is 57 mice ED$_{50}$.

EXAMPLE 2

Neurotoxin Detoxification and Vaccine Preparation

A 900 ml aliquot of the above obtained neurotoxin solution is incubated for one hour at room temperature with 4.8 ml of a solution of 25 g of glutaraldehyde in 100 ml or pyrogen-free distilled water. After that reaction time, the reaction is stopped by addition of one ml of a solution of 48 mg of L-lysine monohydrochloride in 10 ml of pyrogen-free distilled water.

The inactivated toxin is supplemented with 446 ml of 2% sterile solution of aluminium hydroxide (Alhydrogel, Superfos Export Co., Copenhagen, Denmark), 446 ml of Sorensen buffer (Na$_2$HPO$_4$ M/10: 22%; KH$_2$PO$_4$ M/10: 78%) and 1.8 ml of a solution of 1 mg of thiomersal in 10 ml of distilled water. The pH is adjusted to 6.3 with sterile 1 N HCl. The mixture is stirred for 48 hrs. at room temperature and in darkness and thereafter centrifuged.

The sediment of centrifugation is isolated and diluted with supernatant to obtain a final volume of 446 ml. The product is distributed into glass vials containing dosage units (i.e. 256 ED$_{50}$) of detoxified neurotoxin or multiples thereof.

For vaccinal use the product is administered by intramuscular or subcutaneous route, the volume of one dosage unit being 2 ml.

EXAMPLE 3

Relationship Between Neurotoxin Inactivation Level and Antigenicity

Following the technique of Example 2 but using different amounts of glutaraldehyde and allowing the reaction between neurotoxin and glutaraldehyde to take place during different times, products with different residual neurotoxin titres—i.e. inactivation levels —were obtained and tested for their protection in mice.

In this trial, the inactivation levels of the different products were assessed by toxicity test (paralysis and mortality due to paralysis) in mice according to the technique described by H. H. Schimmelpfennig in Fortschr. Vet. Med. 13:49–50, 1970 and their respective protection level in mice was assessed by intravenous administration of a dosage unit of 0.45 ED$_{50}$ per mouse followed, 6 days later, by an intravenous challenge administration of 2.8 ED$_{50}$ of neurotoxin per mouse.

The results are given in Table I and indicate that protection is associated to a toxin inactivation level comprised between about 50% and about 90%.

TABLE I

Antigenicity vs. neurotoxin inactivation level

| Contact Glutaraldehyde (GT) concentration | Time | Neurotoxin titre (x) Residual in GT-treated toxin | Control: non treated toxin | Neurotoxin Inactivation % | Protection in mice (xx) |
| --- | --- | --- | --- | --- | --- |
|  | 5' | <4 |  | >90 | 0 (4/5) |
| 0.052 M | 30' | <4 |  | >90 | 0 (4/5) |
|  | 1 h | <4 |  | >90 | 0 (4/5) |
|  | 2 h | <4 | 39 | >90 | 0 (5/5) |
|  | 5' | <4 |  | >90 | 0 (5/5) |
| 0.026 M | 30' | <4 |  | >90 | 0 (5/5) |
|  | 1 h | <4 |  | >90 | 0 (5/5) |
|  | 2 h | <4 |  | >90 | 0 (5/5) |
|  | 5' | 22.3 |  | 54 | 100 (0/5) |
| 0.013 M | 30' | 14.1 |  | 71 | 100 (0/5) |
|  | 1 h | 5.6 |  | 88 | 100 (0/5) |
|  | 2 h | 5.6 | 48.5 | 88 | 60 (2/5) |
|  | 5' | 44.7 |  | 8 | 100 (0/5) |
| 0.065 M | 30' | 44.7 |  | 8 | 100 (0/5) |
|  | 1 h | 44.7 |  | 8 | 100 (0/3) |
|  | 2 h | 24.3 |  | 50 | 100 (0/5) |

(x) expressed in ED$_{50}$ per intravenous administration
(xx) expressed in percent (number of paralyzed animals/number of tested animals)

EXAMPLE 4

Immune Response in Piglets

Dosage units of the vaccine of Example 2 (256 $ED_{50}$ in 2 ml) were administered either by subcutaneous or intramuscular route to 3 groups of seven 7 day old piglets (named groups Ia, Ib and II) and a booster with the same dosage units was administered two weeks later by subcutaneous route to groups Ia and by intramuscular route to group Ib and one week later by intramuscular route to group II.

When 5 week old, a challenge inoculation of crude neurotoxin was administered by intravenous route to each piglet, the challenge dosage being 2.2 $ED_{50}$ per kg of body weight for the piglets of group Ia and 1.1 $ED_{50}$ per kg of body weight for the piglets of groups Ib and II.

Control groups, named control group Ia and control group Ib/II of 5 week old piglets, were given by intravenous route the same challenge dosage as for groups Ia, and groups Ib and II respectively.

All piglets were kept under control for nervous symptoms (ataxia, convulsions, paralysis) and mortality for one week. Blood samples were taken before and after vaccination and detection of anti-neurotoxin antibodies was performed by seroneutralization test in Vero cells. For that purpose, sera are heated at 56° for 30 minutes and serial two fold dilutions in tissue culture maintenance medium are incubated at 37° C. for one hour in the presence of an equal volume of a standard neurotoxin at a predetermined dilution, which produces a cytotoxic effect in about 50% of Vero cells ($\geq 50\%$).

Duplicate 0.2 ml samples of the toxin-serum mixtures are incubated with cell monolayers for 24 hours at 37° C. and the end point of antitioxin titration is expressed as the reciprocal of the last dilution of serum which inhibits the cytotoxic effect of the standard toxin.

The results obtained for each piglet and for each group are given in the following Table II. No adverse reactions were detected after vaccination.

TABLE II

Immunogenicity of the detoxified neurotoxin against oedema disease in piglets.

| Group | Piglet No. | After challenge inoculation Nervous symptoms | After challenge inoculation Mortality | Anti-neurotoxin antibody titre (x) before vaccination | Anti-neurotoxin antibody titre (x) after vaccination |
|---|---|---|---|---|---|
| Ia | 234 | − | − | 0 | 1 |
|  | 235 | − | + | 0 | 0 |
|  | 236 | − | − | 0 | 2 |
|  | 237 | + | + | 0 | 0 |
|  | 238 | − | − | 0 | 2 |
|  | 239 | + | + | 0 | 0 |
|  | 240 | − | − | 0 | 2 |
|  | Whole group | 2/7 (28%) | 3/7 (43%) | Seroconversion: 4/7 (57%) | |
| Control Ia | 230 | + | + | 0 | 0 |
|  | 231 | + | + | 0 | 0 |
|  | 233 | + | + | 0 | 0 |
|  | 227 | + | + | 0 | 0 |
|  | 228 | + | + | 0 | 0 |
|  | 23 | + | + | 0 | 0 |
|  | Whole group | 6/6 (100%) | 6/6 (100%) | Seroconversion: 0/6 (0%) | |
| Ib | 266 | − | − | 0 | 2 |
|  | 267 | − | − | 0 | 4 |
|  | 268 | − | − | 0 | 2 |
|  | 269 | − | − | 0 | 1 |
|  | 270 | + | − | 0 | 0 |
|  | 271 | − | − | 0 | 0 |
|  | 272 | − | − | 0 | 0 |
|  | Whole group | 1/7 (14%) | 0/7 (0%) | Seroconversion: 4/7 (57%) | |
| II | 283 | − | + | 0 | 0 |
|  | 284 | − | − | 0 | 8 |
|  | 285 | − | − | 0 | 0 |
|  | 286 | − | − | 0 | 0 |
|  | 287 | − | − | 0 | 0 |
|  | 288 | − | − | 0 | 0 |
|  | 289 | − | − | 0 | 0 |
|  | Whole group | 0/7 (0%) | 1/7 (14%) | Seroconversion: 1/7 (14%) | |
| Control Ib/II | 273 | + | − | 0 | 0 |
|  | 290 | + | − | 0 | 0 |
|  | 51 | + | + | 0 | 0 |
|  | 52 | + | − | 0 | 0 |
|  | 53 | − | − | 0 | 0 |
|  | 54 | + | − | 0 | 0 |
|  | 55 | + | − | 0 | 0 |
|  | 56 | + | + | 0 | 0 |
|  | 275 | + | − | 0 | 0 |
|  | 276 | + | − | 0 | 0 |
|  | 277 | + | − | 0 | 0 |
|  | 278 | − | − | 0 | 0 |
|  | 280 | − | − | 0 | 0 |
|  | 281 | + | − | 0 | 0 |
|  | Whole group | 11/14 (79%) | 2/14 (14%) | Seroconversion: 0/14 (0%) | |

(x) Reciprocal of last active serum dilution.

The figures of Table II indicate that in very young piglets an excellent immune response is obtained with a vaccination scheme comprising 2 injections of 256 $ED_{50}$ at a 2 week interval.

The protection provided was 57% against a dose lethal in 100% of the challenged control animals and 82% against a dose inducing in two groups of challenged animals a mortality and a morbidity of 14 and 79% respectively.

From Table II it also appears that the protection against oedema disease is in close correlation with the seroconversion rate (57%) which is significantly different from the seroconversion rate of the control animals and that the vaccination scheme involving two injections at a one week interval is less efficient.

EXAMPLE 5

Immune Response Provided with Detoxified Neurotoxin in 5–8 Week Old Piglets

Dosage units and subunits of vaccine preparation of Example 2 were administered by subcutaneous route to 2 groups of 5–8 week old piglets with a booster administration 3 weeks later and two other groups of 5–8 week old piglets were treated in the same way with neurotoxin adsorbed on Alhydrogel in the same conditions.

The anti-neurotoxin antibody titres after vaccination were determined by seroneutralization in Vero cells 14 days after the booster administration.

The vaccination scheme and the obtained results are summarized in Table III indicating a good seroconversion level after administration of the detoxified neurotoxin.

TABLE III

Seroconversion of piglets vaccinated with detoxified neurotoxin

| Vaccine | Vaccination scheme | Number of animals | Number of sero-converters | Post-vaccinal anti-neurotoxin titre (x) |
|---|---|---|---|---|
| neurotoxin | .2 × 64 ED$_{50}$ at 3 weeks interval | 2 | 1 | 4:0 |
|  | .2 × 256 ED$_{50}$ at 3 weeks interval | 5 | 4 | 2:0:8:4:64 |
| Detoxified neurotoxin | .2 × 64 ED$_{50}$ at 3 weeks interval | 2 | 1 | 8/16:0 |
|  | .2 × 256 ED$_{50}$ at 3 weeks interval | 3 | 3 | 4:2:16 |

(x) Reciprocal of last active serum dilution

I claim

1. A detoxified, highly immunogenic *E. coli* neurotoxin consisting in *E. coli* neurotoxin showing a substantial but inferior to 90% inactivation level obtained by bringing *E. coli* neurotoxin into contact with glutaraldehyde.

2. A detoxified *E. coli* neurotoxin according to claim 1 wherein the inactivation level is comprised between 50 and 90%.

3. A vaccine against oedema disease of piglets comprising an effective dose of a detoxified *E. coli* neurotoxin according to claim 1 or 2.

4. A vaccine against oedema disease of piglets comprising an effective dose of a detoxified *E. coli* neurotoxin according to claim 1 or 2 adsorbed on an effective amount of an adjuvant selected from the group comprising aluminium hydroxide and aluminium phosphate.

5. A method of preventing piglet oedema disease comprising administering to piglets a vaccine according to claim 3.

6. A method of preventing piglet oedema disease comprising administering to piglets a vaccine according to claim 4.

* * * * *